United States Patent [19]  [11] 4,294,713
Knollmueller et al. [45] Oct. 13, 1981

[54] GREASE COMPOSITIONS CONTAINING SELECTED SHIELDED POLYSILICATE COMPOUNDS

[75] Inventors: Karl O. Knollmueller, Hamden; Robert J. Fairbrother; David F. Gavin, both of Cheshire, all of Conn.

[73] Assignee: Olin Corporation, New Haven, Conn.

[21] Appl. No.: 135,744

[22] Filed: Mar. 31, 1980

[51] Int. Cl.³ .................... C10M 5/26; C10M 7/48; C10M 7/50
[52] U.S. Cl. ........................ 252/28; 252/25; 252/29; 252/49.6; 252/40.7
[58] Field of Search ............. 252/28, 25, 29, 49.6, 252/40.7, 42.1

[56] References Cited

U.S. PATENT DOCUMENTS

| | | | |
|---|---|---|---|
| 3,344,066 | 9/1967 | Schiefer et al. | 252/28 |
| 3,518,189 | 6/1970 | Christian | 252/28 |
| 3,526,594 | 9/1970 | Meghir | 252/28 |
| 3,835,050 | 9/1974 | Green | 252/28 |
| 3,965,135 | 6/1976 | Knollmueller | 252/78.3 |
| 3,965,136 | 6/1976 | Knollmueller | 252/78.3 |
| 3,992,429 | 11/1976 | Knollmueller | 252/78.3 |
| 4,048,083 | 9/1977 | Knollmueller | 252/78.3 |
| 4,048,084 | 9/1977 | Knollmueller | 252/78.3 |
| 4,058,546 | 11/1977 | Knollmueller | 252/78.3 |
| 4,077,993 | 3/1978 | Knollmueller | 556/451 |
| 4,086,260 | 4/1978 | Knollmueller | 252/78.3 |
| 4,116,847 | 9/1978 | Knollmueller | 252/78.3 |
| 4,132,664 | 1/1979 | Knollmueller | 252/78.3 |
| 4,175,049 | 11/1979 | Knollmueller | 252/78.3 |

*Primary Examiner*—Delbert E. Gantz
*Assistant Examiner*—Irving Vaughn
*Attorney, Agent, or Firm*—William A. Simons; Thomas P. O'Day

[57] ABSTRACT

Novel grease compositions are described which comprise:

(a) A major amount of a shielded polysilicate compound selected from the group consisting of alkoxysilane cluster compounds, alkoxysilanol cluster compounds, alkoxysilane ester compounds, alkoxysilane multiple cluster compounds, silicone-bridged alkoxysilane double cluster compounds, distillation residues containing these compounds and mixtures thereof; and (b) an amount of at least one grease thickener sufficient to thicken said shielded polysilicate compound to a grease consistency.

28 Claims, No Drawings

GREASE COMPOSITIONS CONTAINING SELECTED SHIELDED POLYSILICATE COMPOUNDS

FIELD OF THE INVENTION

The present invention relates to grease compositions which contain shielded polysilicate compounds as the base fluids.

DESCRIPTION OF THE PRIOR ART

A great variety of high performance greases are known to the art. In particular, a great number of different base fluids for greases are known. For example, many organopolysiloxane fluids, silicone fluids, polyalkylene glycols and their derivatives, high molecular weight esters of dicarboxylic acids and perfluoro polymeric fluids have been employed. Furthermore, a wide variety of organic and inorganic thickeners for greases are known. For example, these include organic thickeners such as alkali metal and alkaline earth soaps, synthetic polymers and the like. Conventional inorganic thickeners for greases include materials such as clay, finely divided silica, silica gel, alumina, graphite, mica, talc and diatomaceous earth. Yet, a need still exists for superior greases which have a combination of properties not met by these known greases. Specifically, it would be desirable to make greases which have a combination of properties including both good low and high temperature viscosity characteristics, good thermal and hydrolytic stabilities and excellent lubricities. The grease compositions of the present invention are believed to fill that need.

Separately, a new class of compounds called shielded polysilicates have been recently discovered which have unusual hydrolytic stability, low volatility, excellent viscosity indexes and have a wide temperature range of use as hydraulic fluids and heat transfer fluids. Furthermore, they do not require the use of additives as is the case of silicones in some comparable situations. But, they do readily accept most conventional additives including antioxidants when necessary. According to the present invention, it has been found that certain of these shielded polysilicate compounds can be admixed with conventional grease thickeners in certain proportions to obtain grease compositions having desirable properties.

BRIEF SUMMARY OF THE INVENTION

Therefore, the present invention is directed to grease compositions comprising:

(a) a major amount of a shielded polysilicate compound selected from the group consisting of alkoxysilane cluster compounds, alkoxysilanol cluster compounds, alkoxysilane ester compounds, alkoxysilane multiple cluster compounds, silicone-bridged alkoxysilane double cluster compounds, distillation residues containing these compounds and mixtures thereof; and (b) an amount of at least one grease thickener sufficient to thicken said shielded polysilicate compound to a grease consistency.

DETAILED DESCRIPTION

The above-mentioned classes of shielded polysilicate cluster compounds form the base fluids for the grease compositions of the present invention. The alkoxysilane cluster compounds and their preparation are fully described in U.S. Pat. Nos. 3,965,136; 4,077,993 and 4,048,084. The alkoxysilanol cluster compounds and their preparation are fully described in U.S. Pat. Nos. 3,965,135 and 4,048,083. The alkoxysilane ester compounds and their preparation are fully described in U.S. Pat. No. 4,086,260. The alkoxysilane multiple cluster compounds and their preparation are fully described in U.S. Pat. Nos. 3,992,429 and 4,132,664. The silicone-bridged alkoxysilane double cluster compounds and their preparation are described in U.S. Pat. Nos. 4,058,546 and 4,116,847. The disclosures of all of these commonly assigned patents are incorporated herein by reference in their entireties.

The use of alkoxysilane cluster compounds, alkoxysilane multiple cluster compounds, and silicone-bridged alkoxysilane double cluster compounds is preferred. Alkoxysilane cluster compounds are particularly preferred. These alkoxysilane clusters have the general formula:

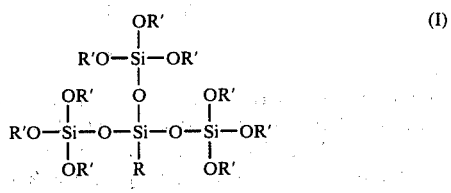

wherein R is hydrogen, alkyl, alkenyl, aryl or aralkyl and each R' is independently selected from the same group as R with the proviso that at least a majority of R' radicals are sterically hindered alkyl groups having at least 3 carbon atoms.

Desirably, R is hydrogen, an alkyl or alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In Formula (I), each R' is independently selected from the same group as R, with the proviso that at least a majority of the R' radicals are sterically hindered alkyl groups having at least 3 carbon atoms. The desired and preferred groups for R' are the same as for R subject to the preceding proviso. Desirably, at least a majority of the R' radicals are sterically hindered alkyl groups having about 3 to about 18 carbon atoms and preferably are sterically hindered alkyl groups having about 4 to about 12 carbon atoms. By sterically hindered alkyl groups is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radical and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, 2,4-dimethyl-3-pentyl, and the like.

The alkoxysilane multiple cluster compounds feature the general formulae:

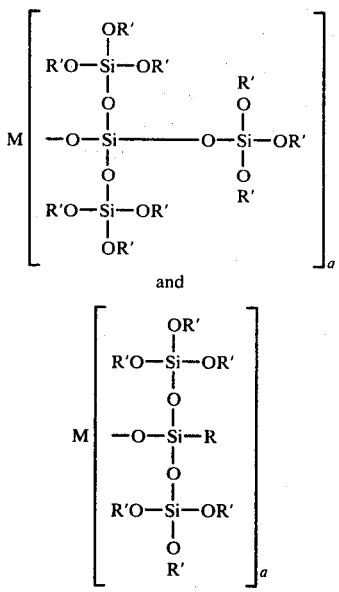

(II)

and

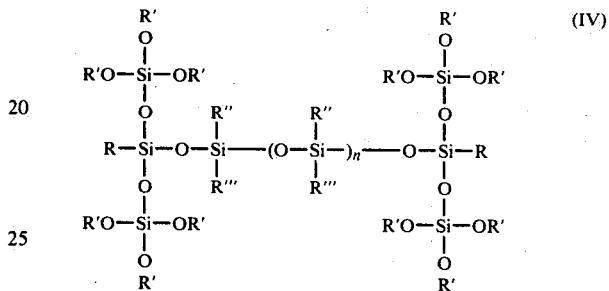

(III)

(IV)

wherein a=2, 3 or 4; M is a substituent branched or straight chain hydrocarbon radical; R is hydrogen, alkyl, alkenyl, aryl or aralkyl and each R' is independently selected from the same group as R with the proviso that at least a majority of R' radicals are sterically hindered alkyl groups having at least 3 carbon atoms.

The compounds used in the present invention are those represented by the above formulae wherein a=2, 3 or 4, as mentioned. Desirably, a=2 or 3 and preferably, a=2. The substituent M is defined as a substituted or unsubstituted hydrocarbon radical, either branched or straight chained. Branched radicals are preferred. By hydrocarbon radical is meant both oxylated radicals and radicals which have not been oxylated. Thus, M may be a straight or branched chain hydrocarbon diradical, triradical or tetraradical containing carbon and hydrogen atoms, with or without inert substituents. Alternatively, M may be a straight or branched chain hydrocarbon diradical, triradical or tetraradical having one or more ether and/or ester units, with our without inert substituents. The radical M is a hydrocarbon radical, as defined, having up to about 25 carbon atoms, desirably having about 2 to about 18 carbon atoms, and preferably having about 4 to about 12 carbon atoms. The hydrocarbon radical may, as mentioned, be unsubstituted or it may be substituted and these substituents include, e.g., hydroxy groups, phenyl groups and any substituents which do not interfere with the hydrolytic stability of the molecule to an undesirable degree.

R is defined as hydrogen, an alkyl, alkenyl, or aryl or aralkyl radical. Desirably, R is hydrogen, an alkyl or alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In the above formulae, each R' is independently selected from the same group as R, with the proviso that at least a majority of the R' radicals are sterically hindered alkyl groups having at least 3 carbon atoms. The desired and preferred groups for R' are the same as for R subject to the preceding proviso. Desirably, at least a majority of the R' radicals are sterically hindered alkyl groups having about 3 to about 18 carbon atoms and preferably are sterically hindered alkyl groups having about 4 to about 12 carbon atoms. By sterically hindered alkyl groups is meant alkyl radicals which contribute to the hydrolytic stability of the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, and 2,4-dimethyl-3-pentyl, and the like.

The silicone-bridged alkoxysilane double cluster compounds have the general formula:

wherein n is an interger from 0 to 300; R is hydrogen, alkyl, alkenyl, aryl, aralkyl or —OSi(OR')₃; each R' is independently selected from alkyl, alkenyl, aryl or aralkyl with the proviso that at least a majority of R' radicals are sterically hindered alkyl groups having at least 3 carbon atoms; and R" and R''' are independently selected from hydrogen, alkyl, alkenyl, aryl, aralkyl, hydroxy-alkyl, and halo- or cyano-substituted alkyl, alkenyl, aryl, aralkyl and hydroxy-alkyl.

As defined above, the group R of the Formula IV compound is hydrogen, alkyl, alkenyl, aryl, aralkyl or —OSi(OR')₃. Preferably, R is hydrogen, alkyl or alkenyl having about 1 to about 18 carbon atoms or aryl or aralkyl having about 6 to about 24 carbon atoms. Most preferably, R is hydrogen, alkyl or alkenyl having about 1 to about 8 carbon atoms or aryl or aralkyl having about 6 to about 14 carbon atoms.

Also as defined above, R' groups of Formula IV are independently selected from alkyl, alkenyl, aryl or aralkyl, with the proviso that at least a majority of the R' radical are sterically hindered alkyl groups having at least 3 carbon atoms. Preferably, at least a majority of the R' radical are sterically hindered alkyl groups having about 3 to about 18 carbon atoms and, most preferably, are all sterically hinderd alkyl groups having about 4 to about 12 carbon atoms. By sterically hindered is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered groups include sec. butyl, isobutyl, 2-ethyl butyl, 2-ethyl pentyl, 3-ethyl pentyl, 2-ethyl hexyl, 3-ethyl hexyl, 2,4-dimethyl-3-pentyl, and the like.

Also preferred for the present invention are the distillation residues which contain these shielded polysilicate compounds. Generally, the last step in the preparation of any of these shielded polysilicate compounds is the distillation of a crude shielded polysilicate product. During this distillation, one or more forecut products are first distilled off. These forecuts normally contain low boiling by-products. Next, the major portion of the desired shielded polysilicate is distilled off. This major portion is normally of a very high purity (i.e., above about 97% by weight) of the desired product. After this major portion is distilled away, a distillation residue is still left undistilled. This distillation residue is usually made up of from about 5% to about 80% by weight or greater of the desired shielded polysilicate product, along with polymeric chains of the shielded polysilicate compounds.

Also, these residues are not usually of sufficient purity to directly employ in conventional uses such as functional fluids. Moreover, the cost of purifying these residues is somewhat prohibitive. Accordingly, it has now been found that these distillation residues that contain various amounts of shielded polysilicates may be advantageously employed in grease compositions and, thus, obviate any disposal problems. Therefore, the present invention contemplates the use of distillation residues containing any of the above-mentioned classes of shielded polysilicates. Of course, it may be desirable to treat these distillation residues to simply remove discolorations, insolubles or traces of acidity before their use in greases. Such treatments include known and standard techniques such as contacting with activated charcoal, clay, filtration or the like.

As stated above, it is contemplated that one or more of the selected shielded polysilicate compounds or the distillation residues containing said compounds will constitute a major amount (i.e., more than about 50% by weight) of the total grease composition. More preferably, it may be desirable to have the grease compositions contain from about 60% to about 95% by weight of these selected shielded polysilicates or distillation residues containing said compounds.

Besides the above-named base fluids, it is necessary that the grease compositions of the present invention contain a suitable amount of one or more grease thickeners in order to obtain a desirable grease consistency. A wide latitude in the selection of thickeners is permitted by the present invention, provided the thickener has no adverse effect on the shielded polysilicate compound. Accordingly, the thickeners may be any of a number of materials used to thicken base fluids to a grease consistency. Specifically, any suitable organic or inorganic grease thickener, or any combination thereof, may be used.

Organic grease thickeners which may be suitable include alkali metal and alkaline earth soaps such as sodium or lithium stearate, sodium or lithium hydroxystearate, calcium or magnesium stearate, or calcium or magnesium hydroxystearate. Other suitable thickeners include synthetic polyureas, organosiloxanes, and mixtures thereof. Suitable amounts of these alkali metal and alkaline earth soaps may range from about 0.01% to about 50%, more preferably from about 0.1% to about 10% by weight of the total grease composition.

Inorganic grease thickeners which may be suitable might include clay, silica, alumina, graphite, mica, talc, diatomaceous earth and mixtures of these materials.

Particularly preferred as a grease thickener for the present invention is finely divided silica, that is, a non-structured silica consisting of discrete, roughly spherical particles rather than chains of silica particles adhering one to the other. It is generally preferred that the particle size of the silica may range in diameter from about 0.005 to 0.02 microns and the surface area may be in the range from about 100 to about 400 $m^2$/gram. Such finely divided silicas may be prepared by various known techniques, including low temperature precipitation from aqueous solutions of soluble silicates, high temperature hydrolysis of silicon tetrachloride or the like. Particularly, suitable for use in this invention has been found to be a high purity silica from Cabot, Corp., of Boston, Mass., under the trademark "Cab-O-Sil M-5". This is a pyrogenic silica prepared by the high temperature hydrolysis of silicone tetrachloride.

Such finely divided silica may be used in grease compositions of the present invention as being either untreated or treated with one or more silylating agents to render their surfaces hydrophobic. Some of these silylating agents are listed in U.S. Pat. Nos. 3,344,066 and 3,526,594, which are incorporated herein by reference in their entireties. Examples of such silylating agents include trimethylchlorosilane, hexamethyl disilazane and bis-trimethylsilyl acetamide. The technique of rendering finely divided silica hydrophobic for grease compositions is well known in the art and the present invention is not to be limited to any particular methods of silylating or with particular silylating agents.

If finely divided silica is employed as a thickener, either untreated or rendered hydrophobic or both, it may generally be used in amounts from about 5% to about 50% by weight of the total grease composition. More preferably, it may be desirable to employ from about 8% to about 18% by weight silica. Also, any ratio of untreated silica to hydrophobic silica is contemplated herein, with the preferred ratio depending on the exact base fluid employed.

The grease compositions of the present invention may contain, if desired, other additives well known to the art without departing from the scope of this invention. For example, such greases may contain corrosion and/or rust inhibitors, E.P. lubricating agents, anti-oxidants, metal deactivators, stabilizers, anti-wear agents, V.I. improves or other viscosity control agents, dyes, bleed reducing agents and the like. The use of such additives and the amounts thereof will, of course, depend upon the conditions to which the grease may be subjected.

The ingredients for making greases of the present invention may be admixed according to conventional grease manufacturing techniques; for example, by the gradual addition of the thickeners to the shielded polysilicate base fluid, while the latter is being mixed in a grease-compounding mill. Such mixing may be continued until the desired consistency is achieved.

The grease products of the present invention may be excellent lubricating greases and may have longlasting stability and good thermal and hydrolytic properties, even when subjected to extremes of temperatures and working conditions.

The following examples further illustrate the present invention. All parts and percentages are by weight unless otherwise explicitly stated.

EXAMPLE A

Preparation Of An Alkoxysilane Cluster—Tris(tri-sec-butoxysiloxy)-Methylsilane

A 5 liter three-neck flask was equipped with a stirrer, reflux condenser, thermometer and an equilibrated dropping funnel. Provisions were made to change from a cooling bath to a heating mantle without disturbing the set up. To prevent moisture from entering, the reflux condensate was topped with a CaCl$_2$ tube, while a slow stream of dry nitrogen was passed through the apparatus via the equilibrated funnel. The flask was charged with 1143 grams (4.325 moles) tri-sec butoxysilanol having the formula [(sec-C$_4$H$_9$O)$_3$-SiOH] and having a 93.7% by weight purity (VPC) and 426 grams (5.39 moles) pyridine in 1200 milliliters of toluene. While being cooled at about 5° C., the flask was next charged with 202 grams (1.351 moles) of methyltrichlorosilane having the formula CH$_3$SiCl$_3$ in 400 milliliters toluene through the dropping funnel over a 2 to 4 hour period. The temperature was then raised to 75° C. and held there for 4 hours. The reaction mixture was again cooled to about 5° C. and 700 milliliters water was added to the cooled reaction mixture. The water addition dissolved all of the pyridine hydrochloride and excess pyridine present in the reaction mixture. These impurities along with some others were then removed by phase separating the organic and aqueous layers. The addition of 700 milliliters water, followed by phase separation, was repeated four more times to give a chloride-free organic layer. Then, the toluene was distilled off (along with any azeotropically entrained water). The last traces of the toluene solvent and pyridine were removed by vacuum stripping. A crude product weighing 1062 grams was left.

This crude product was then fractionated in vacuo using a Spinning Band Column. The forecut consisted of by-products of the reaction, weighing 279 grams. It was collected as boiling from temperatures ranging from 80° C. to 191° C. at 0.05 mm Hg. The major amount of the desired alkoxysilane cluster product was collected at 191° C. to 192° C. at 10.05 mm Hg and weighed 690 grams.

The distillation residue weighed 93 grams and consisted of 11% by weight of the undistilled desired alkoxysilane cluster product, along with a mixture of by-products and polymeric condensation products of the desired alkoxysilane cluster product. This distillation residue was brown colored and the following clean-up procedure was used to remove that brown color (removal was necessary for a clean looking grease).

First, a reaction flask was charged with 396 grams of the distillation residues of several preparations made by the procedure stated above. Next, 7.9 grams of active carbon and 7.9 grams of Attaclay were added to the flask. The mixture was kept blanketed with nitrogen, while it was heated for 3 hours at 100° C. Some water bound in the Attaclay escaped during this heating phase. The contents were filtered through a filter which was packed 1 cm. high with Celite filter aid in order to catch the fine carbon particles. During filtration, the funnel was heated with an electric heating tape to about 50° C. to 60° C. in order to speed up the filtration of the viscous fluid. A light yellow material was thus obtained, which weighed 390 grams. Its analytical composition was: C: 42.92%; H: 9.34%; Si: 15.25%.
Furthermore, this distillation residue was characterized by the following properties:

| | |
|---|---|
| Viscosity @ 210° F. | 16.77 cst. |
| Viscosity @ 100° F. | 70.26 cst. |
| Viscosity @ −40° F. | 3240. cst. |
| Viscosity @ −65° F. | 11958. cst. |
| Extended Viscosity Index (V.I.) | 285 |

| -continued | |
|---|---|
| Pour Point | −110° F. |
| Density @ 24° C. | .9955 |
| Refractive Index | 1.4195 |
| Wear Scar by 4 ball test at 1200 rmp (40 Kg and 167° F. for 1 hour) | .57 mm |
| Evaporation loss (thin film) (1 gram in dish of 2″ dia.) | |
| @ 400° F. for 1 hour | 3.9% |
| @ 300° F. for 100 hours | 1.0% |

EXAMPLE B

Preparation of Alkoxysilane Multiple Cluster—1,3-[bis-(tri-sec-butoxysiloxy) methyl-siloxy]-2,2-dimethyl propane A 5 liter three-neck flask was equipped with a stirrer, reflux condenser, thermometer and an addition funnel. A solution of 1700.7 grams of bis(tri-sec-butoxysiloxy) methylchloride silane CH$_3$(Cl)Si[OSi(OC$_4$H$_9$)$_3$]$_2$, which assayed at 82.69% (corresponding to 1406.3 grams (2.33 moles) of the compound), in 2.4 liters of heptane was charged into the flask. A solution of 120.9 grams (1.16 mole) neopentyl glycol in 300 grams (3.79 moles) pyridine was next added through the dropping funnel during a 15 minute period. The temperature rose from about 25° C. to 32° C. The dropping funnel was then replaced by gas addition stopcock to admit a dry nitrogen blanket to the flask. The mixture was then refluxed for 16 hours.

Next, the reflux was stopped and the flask was allowed to cool at room temperature. Then, 1 liter of water was added into the cooled flask to dissolve the pyridine hydrochloride and some of the excess pyridine. The formed aqueous and organic layers were then phase separated. The water addition (500 ml each time) followed by the phase separation step was repeated four more to obtain a chloride-free organic layer. Next, the heptane was distilled off with any remaining wash water. Then, the last traces of heptane solvent and pyridine were removed by vacuum stripping and a crude product weighing 1689 grams was obtained.

This crude product was fractionally distilled on a Vigreux Column. The forecut consisted of by-products of the reaction, weighing 461 grams, was collected as boiling at temperatures from 152° to 258° C. at 0.07 mm Hg. The major portion of the desired neopentyl glycol double cluster was collected as boiling at 258° C. ±2° C. at 0.07 mm Hg. The major cut weighed 889.5 grams (yield: 61.4% by weight). The distillation residue weighed 236 grams while 100 grams light by-products were found in a trap.

EXAMPLE C

Surface Treatment of Cab-O-Sil M5

A 5 liter three-neck flask was equipped with a stirrer, reflux condenser and thermometer. Through a side arm of the thermometer adaptor, a nitrogen blanket could be maintained in the apparatus. The apparatus was charged with 93 grams of Cab-O-Sil M5 finely divided silica, suspended in 2800 ml toluene. Next, 2 ml of hexamethyl disilazane was added and the stirred mixture heated to reflux for 2 hours. The reflux condenser was now substituted with a condenser and a Claisen head. Then, most of the solvent and unreacted silylating agent was thus removed by distillation. Residual solvent was stripped in vacuo. The hydrophobic Cab-O-Sil M5 was scraped off the walls and the lumpy conglomerates were crushed in a mortar with a pestle.

Method D2225-72. As seen in Table I, none of the greases made in Examples 1-9 had a drop point.

TABLE I

| Example | Example A Product | Example B Product | Distillation Residue of Example A | Surface Treated Cab-O-Sil M5 | Untreated Cab-O-Sil M5 | Silicone Oil | Penetration Value | Wear (5kg) Scar (mm) | Drop Point |
|---|---|---|---|---|---|---|---|---|---|
| 1 | 36 grams | — | — | 6 grams | — | 0 | 330 mm | 0.68 mm | None |
| 2 | 36 | — | — | 7.5 | — | 2.5 grams | 260 mm | 0.56 mm | None |
| 3 | 36 | — | — | 7 | — | 2 | 336 mm | 0.68 mm | None |
| 4 | 34.02 | — | — | 8.46 | — | 0 | 129 mm | 0.73 mm | None |
| 5 | — | 36.2 grams | — | 6.0 | 1.0 grams | 0 | 199 mm | 0.65 mm | None |
| 6 | — | 40 | — | 6.0 | 1.0 | 1 | 388 mm | 0.87 mm | None |
| 7 | — | 34 | — | 6.72 | 1.26 | 0 | 309 mm | 0.98 mm | None |
| 8 | — | — | 34 grams | — | 6 | 2 | 142 mm | 0.62 mm | None |
| 9 | — | — | 36 | — | 6 | 3 | 486 mm | 0.9 mm | None |

EXAMPLES 1-9

Part I: Preparation of Greases

A Sigma Blade Laboratory Mixer, Model 4LP (Atlantic Research Co.) modified with an alternate steam heating/water cooling jacket was employed for these Examples.

In all of these Examples, various amounts of either the desired major product of Example A or B or the distillation residue of Example A were placed in the mixer first. See Table I for these amounts. Next, while at room temperature, various amounts of untreated Cab-O-Sil M5 finely divided silica, substantially hydrophobic Cab-O-Sil M5 finely divided silica as prepared by the procedure in Example C, and dimethylsilicone oil of 350 cst. viscosity were gradually milled into the mixer. Also See Table I for those amounts. After a completely homogeneous phase was obtained, the milling was continued for 15 more minutes at room temperature. Total cold mixing time was usually around 30-40 minutes. The milling was then stopped and the mill was heated by the steam jacket to about 200° F. to about 230° F. for 30 minutes. The mixture was then milled at that temperature for about 5 minutes. After this time period, the mixture was allowed to cool to room temperature and milled again at room temperature for about 2 minutes.

The greases made in these Examples were tested for consistency by the test described in ASTM 1403-310, converted as described to the full scale cone penetration test of ASTM D217-68. Briefly, this test measures the depth that a cone-shaped weight sinks into a grease. Specifically, the tests consists of measuring the penetration in mm of that test weight (having specified dimensions and weight) into a grease during a 5-second interval. Low "penetration" values therefore indicate a thick grease, and high values indicate a thin grease. A penetration of over 400 mm indicates that the material is more soup-like than grease-like, whereas a "penetration" of less than 100 mm indicates that the grease is too thick to be normally used. The penetration values for each Example are given in Table I. All of these penetration values are for unworked greases.

The lubricity of greases was measured by the 4-ball method described as ASTM Method D2266-67. As with tests on lubricating oils, the wear scar in mm is measured on three steel test balls. The wear scar results are also given in Table I.

Finally, the drop point of the grease made in Examples 1-9 were tested. The drop point of a grease is the temperature at which a grease begins to drop from a small test funnel. The test is described in ASTM

What is claimed is:
1. A grease composition comprising:
(a) a major amount of a shielded polysilicate compound selected from the group consisting of alkoxysilane cluster compounds, alkoxysilanol cluster compounds, alkoxysilane ester compounds, alkoxysilane multiple cluster compounds, silicone-bridged alkoxysilane double cluster compounds, distillation residues containing these compounds, and mixtures thereof; and
(b) an amount of at least one grease thickener sufficient to thicken said shielded polysilicate compound to a grease consistency.
2. The composition of claim 1 wherein said shielded polysilicate compound is selected from the group consisting of:
(a) alkoxysilane cluster compounds having the general formula:

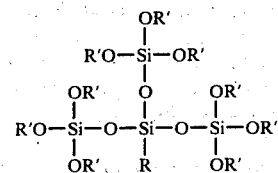

wherein R is hydrogen, alkyl, alkenyl, aryl or aralkyl and each R' is independently selected from the same group as R with the proviso that at least a majority of R' radicals are sterically hindered alkyl groups having at least 3 carbon atoms;
(b) alkoxy silane multiple cluster compounds having a formula selected from the formulae:

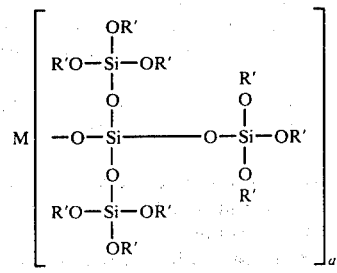

and

-continued

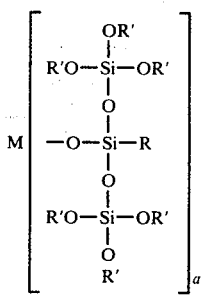

wherein a=2, 3 or 4; M is a substituent branched or straight chain hydrocarbon radical; R is hydrogen, alkyl, alkenyl, aryl or aralkyl and each R' is independently selected from the same group as R with the proviso that at least a majority of R' radical are sterically hindered alkyl groups having at least 3 carbon atoms; and (c) silicone-bridged alkoxysilane double cluster compounds having the formula:

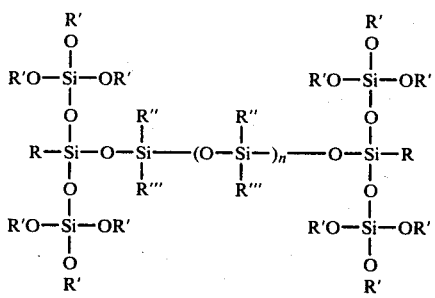

wherein n is an integer from 0 to 300; R is hydrogen, alkyl, alkenyl, aryl, aralkyl or $-OSi(OR')_3$; each R' is independently selected from alkyl, alkenyl, aryl or aralkyl with the proviso that at least a majority of R' radicals are sterically hindered alkyl groups having at least 3 carbon atoms; and R'' and R''' are independently selected from hydrogen, alkyl, alkenyl, aryl, aralkyl, hydroalkyl, and halo or cyano-substituted alkyl, alkenyl, aryl, aralkyl, and hydroalkyl.

3. The composition of claim 2 wherein said shielded polysilicate compound is an alkoxysilane cluster compound.

4. The composition of claim 3 comprising an alkoxysilane cluster compound wherein R is hydrogen, alkyl or alkenyl having about 1 to about 18 carbon atoms or aryl or aralkyl having about 6 to about 24 carbon atoms.

5. The composition of claim 4 comprising an alkoxysilane cluster compound wherein R is hydrogen, alkyl or alkenyl having about 1 to about 8 carbon atoms or aryl or aralkyl having about 6 to about 14 carbon atoms.

6. The composition of claim 5 wherein said alkoxysilane cluster compound is tris(tri-sec-butoxysiloxy)methylsilane.

7. The composition of claim 2 wherein said shielded polysilicate compound is an alkoxysilane multiple cluster compound.

8. The composition of claim 2 wherein said shielded polysilicate compound is a silicone-bridged alkoxysilane double cluster compound.

9. The composition of claim 1 wherein the amount of said shielded polysilicate compound is in the range from about 60% to about 95% by weight of the total grease composition.

10. The composition of claim 1 wherein at least a proportion of said grease thickener is an inorganic material selected from the group consisting of clay, silica, alumina, graphite, mica, talc, diatomaceous earth and mixtures thereof.

11. The composition of claim 10 wherein said inorganic material is finely divided silica having a surface area from about 100 to about 400 m$^2$/gram.

12. The composition of claim 11 wherein at least a proportion of said finely divided silica has had its surface rendered hydrophobic.

13. The composition of claim 11 wherein the amount of said finely divided silica ranges from about 5% to about 40% by weight of the total grease composition.

14. The composition of claim 13 wherein the amount of said finely divided silica ranges from about 8% to about 18% by weight of the total grease composition.

15. The composition of claim 1 wherein at least a portion of the thickener is an organic material selected from the group consisting of alkali metal and alkaline earth soaps, synthetic polyureas and organosiloxanes and mixtures thereof.

16. The composition of claim 15 wherein the organic material is alkali metal and alkaline earth soaps selected from the group consisting of sodium stearate, lithium stearate, sodium hydroxystearate, lithium hydroxystearate, calcium stearate, calcium hydroxystearate, magnesium stearate, magnesium hydroxystearate, and mixtures thereof.

17. The composition of claim 16 wherein the amount of said alkali metal and alkaline earth soaps ranges from about 0.1% to about 10% by weight of the total grease composition.

18. The composition of claim 1 which additionally contains at least one silicone oil.

19. The composition of claim 18 wherein the amount of said silicone oil ranges from about 0.1% to about 10% by weight of the total grease composition.

20. The composition of claim 1 wherein said shielded polysilicate is tris(tri-sec-butoxysiloxy)methylsilane and said grease thickener is finely divided silica.

21. The composition of claim 20 wherein the amount of said tris(tri-sec-butoxysiloxy)methylsilane ranges from about 60% to about 95% by weight of total grease composition and the amount of said finely divided silica ranges from about 45% to about 5% by weight of the total grease composition.

22. The composition of claim 21 which additionally contains silicone oil.

23. The composition of claim 21 wherein at least a portion of said finely divided silica has had its surface rendered hydrophobic.

24. The composition of claim 23 which additionally contains silicone oil.

25. The composition of claim 1 wherein said shielded polysilicate is 1,3-(Bis-(tri-sec-butoxysiloxy)methylsiloxy)-2,2-dimethyl propane.

26. The composition of claim 1 wherein said shielded polysilicate compound is contained in a distillation residue.

27. The composition of claim 26 wherein said distillation residue contains an alkoxysilane cluster compound.

28. The composition of claim 27 wherein said alkoxysilane cluster compound is tris(tri-sec-butoxysiloxy)methylsilane.

* * * * *

UNITED STATES PATENT AND TRADEMARK OFFICE
CERTIFICATE OF CORRECTION

PATENT NO. : 4,294,713
DATED : October 13, 1981
INVENTOR(S) : Knollmueller et al It is certified that error appears in the above-identified patent and that said Letters Patent are hereby corrected as shown below:

In column 6, at line 30, delete "50%" and insert therefor --40%--;
at line 42, delete "improves" and insert therefor --improvers--.

In column 9, at line 38, delete "200°F." and insert therefor --220°F.--.

Signed and Sealed this

Fifteenth Day of June 1982

[SEAL]

Attest:

GERALD J. MOSSINGHOFF

Attesting Officer

Commissioner of Patents and Trademarks